Figure 1:
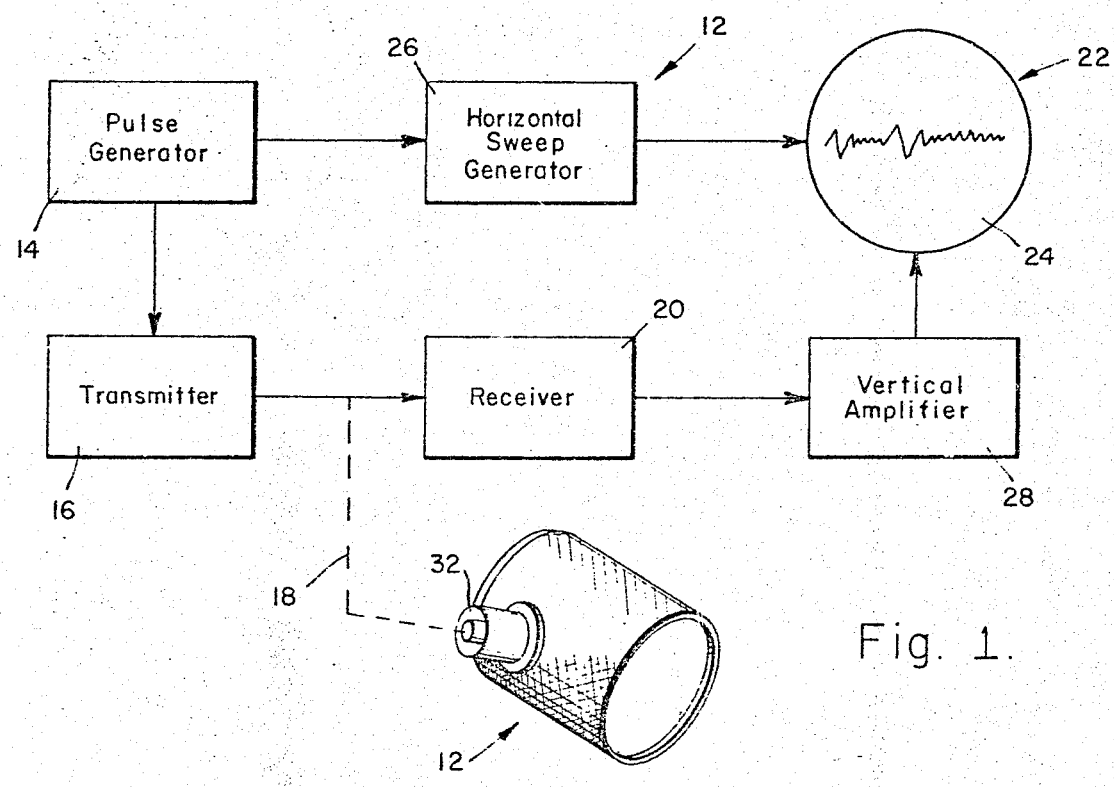

United States Patent [19]
McElroy

[11] 3,950,660
[45] Apr. 13, 1976

[54] ULTRASONIC CONTACT-TYPE SEARCH UNIT

[75] Inventor: Jerry T. McElroy, Boulder, Colo.

[73] Assignee: Automation Industries, Inc., Los Angeles, Calif.

[22] Filed: Nov. 8, 1972

[21] Appl. No.: 304,740

[52] U.S. Cl. .................. 310/9.1; 310/3.2; 310/8.7; 73/67.5 R; 73/71.5 US
[51] Int. Cl.² .................................................. H01L 41/08
[58] Field of Search ............... 310/8.2, 8.7, 8.9, 9.1; 73/67.5 R, 71.5 US; 340/8 MM, 8 RT

[56] References Cited
UNITED STATES PATENTS

| | | | |
|---|---|---|---|
| 2,671,862 | 3/1954 | Farrow | 310/8.7 X |
| 2,875,354 | 2/1959 | Harris | 310/8.2 |
| 2,956,185 | 10/1960 | Von Stocker | 310/8.7 |
| 3,068,370 | 12/1962 | McInnish | 310/8.7 |
| 3,303,691 | 2/1967 | Beaujard et al. | 310/8.7 X |
| 3,379,051 | 4/1968 | Zeutschel et al. | 73/67.5 R |
| 3,387,149 | 6/1968 | Young | 310/8.7 X |
| 3,427,481 | 2/1969 | Lenahan et al. | 310/8.2 |

*Primary Examiner*—Mark O. Budd
*Attorney, Agent, or Firm*—Dan R. Sadler

[57] ABSTRACT

An ultrasonic nondestructive testing system and a contact-type, ultrasonic search unit for use in connection therewith are disclosed. The ultrasonic search unit includes a transducer crystal for receiving and transmitting ultrasonic energy, a housing in which the crystal is mounted, a dampening backing compound, and a wear-resistant cylindrical member or ring disposed within the housing and in which the crystal is mounted to provide a hard, durable, long-lasting contact face.

10 Claims, 2 Drawing Figures

ULTRASONIC CONTACT-TYPE SEARCH UNIT

BACKGROUND

In an ultrasonic nondestructive testing system, there may be provided one or more search units for transmitting ultrasonic energy into a workpiece in response to a driving signal, receiving ultrasonic energy reflected from the workpiece, and producing electrical signals corresponding to the energy received for subsequent display and evaluation.

In one testing system with which the present invention may be advantageously employed the pulse-echo technique of energy transmission and reception is used wherein the search unit transmits bursts or pulses of ultrasonic energy into a workpiece in response to periodic driving signals. The ultrasonic energy directed into the workpiece will be reflected back to the search unit from any discontinuities in either the surface or interior of the workpiece including cracks, voids, inclusions and the like. These received ultrasonic energy echos generate electrical signals which correspond to the echos and by measuring the amplitude and time delay of the electrical signals, the size and position of a discontinuity may be determined.

The testing system above described may be generally employed for two distinct types of testing methods: (1) contact testing or (2) immersion testing. In the contact form of testing, the face of the search unit from which the ultrasonic energy is propagated is placed in direct contact with the surface of the workpiece and such contact must be intimate to assure proper acoustic coupling between the workpiece and the crystal. In immersion testing, the search unit and workpiece are normally completely submerged in a tank of fluid, such as water, and while the face of the search unit is spaced from the workpiece, it is acoustically coupled thereto by the fluid.

The search unit of the present invention is particularly adapted for use in contact-type testing. Presently available search units used for contact testing employ a steel housing of generally cylindrical construction in which the crystal is mounted such that the face of the crystal is substantially coplanar with the annular end of the steel housing. A hard facing material, such as aluminum oxide, may be deposited or otherwise produced on the face of the crystal to protect the face against wear due to the abrasion encountered when the search unit is being moved relative to the workpiece surface and in intimate contact therewith. Such devices are not entirely satisfactory. Although the facing material may have good abrasion resistance, the steel annular end of the housing tends to wear away relatively rapidly. When this occurs at least a portion of the face of the crystal protrudes from the housing. The protrusion of the crystal exposes the circumferential edge of the crystal which has been found to result in fracture due to impact in the normal handling of the search unit. Such fracture of both the facing and crystal material may partially or completely destroy proper functioning of the search unit necessitating replacement of the unit.

Moreover, the crystal facing material used on these commercially available units is expensive and the use of a relatively abrasive resistant housing, such as steel, also increases the overall cost of manufacture of the search units.

SUMMARY

The present invention provides means of overcoming the foregoing difficulties. More particularly, the present embodiment of the invention includes a contact-type search unit having a housing with an inner, extremely hard, abrasion-resistant, ceramic ring in which the crystal is mounted. During use, where the face of the search unit during normal operation is repeatedly in engagement with the workpiece surface, the ceramic ring will provide a contact or wear face. This protects the crystal from abrasion or fracture but at the same time permits the use of a low cost material for the search unit housing as well as a low cost facing material for the crystal.

DRAWING

Figure 2:
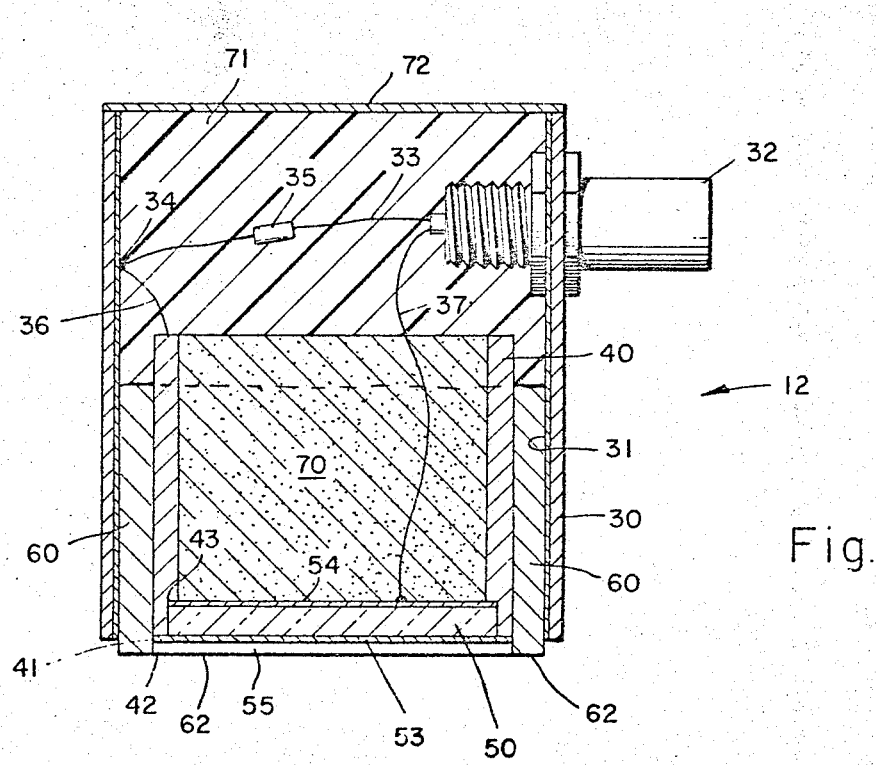

FIG. 1 is a block diagram of a nondestructive testing system employing a contact-type search unit constructed in accordance with the present invention; and FIG. 2 is a cross-sectional view of an exemplary embodiment of the contact-type search unit shown in FIG. 1.

DESCRIPTION

Referring now to the drawing, and more particularly to FIG. 1, there is shown an ultrasonic nondestructive testing system 10 in which the ultrasonic contact-type search unit 12 of the present invention may be employed. The ultrasonic nondestructive testing system 10 in the exemplary embodiment may be of the so-called pulse-echo system although it will be understood that the search unit 12 of the present invention may be used in a continuous wave, pulsed, or other type of system. It will also be understood that a testing system, depending upon its application, may include one search unit of the type herein described as a transmitter and an identical second unit as a receiver or the system may employ a single unit which functions both as transmitter and receiver.

The conventional pulse-echo nondestructive testing ultrasonic system 10, shown in FIG. 1, includes a pulse generator 14 which produces a series of repeated or periodically occuring clock or timing pulses. These timing pulses are effective to determine the repetition rate at which the system operates. While such repetition rate is not a critical part of the present invention, and may vary over a wide range, an exemplary rate is approximately 1 kilocycle per second.

Coupled to the output of the pulse generator is a pulser or transmitter 16 which is responsive to the timing pulses of the generator. The transmitter will thus operate synchronously with the pulse generator. Each time a timing pulse is generated, the transmitter 16 will produce a suitable pulse for driving the search unit 12. Such pulse is normally a high voltage signal of radio frequency in a range of 25 kilocycles to 25 megacycles or higher. The pulse may persist for a single cycle or less or, alternatively, it may include a limited number of cycles such as 5 to 10 or even more cycles per pulse.

The transmitter 16 is coupled to the search unit 12 such as through a flexible, coaxial cable 18 so that the search unit 10 is portable and easily movable by the operator so that it may be properly coupled to a workpiece.

Each driving pulse applied to the search unit 10 produces a burst or pulse of ultrasonic energy transmitted from the search unit into the workpiece. If the workpiece includes a discontinuity, such imperfection acts as a reflector so that the ultrasonic pulses which strike the imperfection will be returned to the search unit as an echo.

The reflected ultrasonic energy which strikes the face of the search unit excites the crystal transducer element producing an electrical signal which is coupled to a receiver 20 by means of the coaxial cable 18. The receiver 20 is effective to receive the electrical signal and provide an output which is coupled to suitable indicating means which may be visual such as a display or other means of temporarily or permanently recording the electrical signal generated by the echo. By way of example, the testing system 10 includes an oscilloscope 22 having a cathode ray tube 24 with horizontal and vertical deflection means.

The system 10 further includes a horizontal sweep generator 26 coupled to the pulse generator 14 and to the horizontal deflection means of the cathode ray tube 24. The horizontal sweep generator is responsive to each timing pulse of the pulse generator to thereby sweep the electron beam horizontally across the face of the cathode ray tube 24.

The output of the receiver 20 is coupled to a vertical deflection amplifier 28 which in turn is coupled to the vertical deflection means in the cathode ray tube 24.

It will therefore be seen that a visual display is created on the face of the cathode ray tube 24. Such display includes a horizontal trace with one or more vertical marks spaced therealong. Such marks correspond to the driving signal originally applied to the search unit 12 and any signals produced by the search unit as a result of its receiving any returning echos of ultrasonic energy. The horizontal displacement of the marks along the trace corresponds to the time of reception of such echo and therefore is a function of the range or distance of the reflector or discontinuity within the workpiece. The amount of the vertical deflection or vertical height of the mark of the trace is a function of the magnitude of the echo and is therefore a function of the size of the reflector or discontinuity.

Directing attention now more specifically to the search unit 12, illustrated in detail in FIG. 2, it will be seen that the unit comprises a generally cylindrical outer shell or housing 30 which may be of any material, preferably light in weight, relatively rigid, durable, and inexpensive. It will be apparent that many types of plastic or similar materials would be suitable for the outer shell or housing 30 such as a paper based phenolic, i.e., paper coated with phenolic. On the inner surface of the outer shell, it is desirable to have a metallic surface 31 for shielding the crystal from stray electromagnetic signals from outside sources which would obviously seriously distort the accuracy of the data acquired through use of the search unit. While various types of shielding may be provided, it has been found that common silver paint coated on the inside surface of the shell and preferably baked on will provide the desired shielding. Obviously, other alternative shielding materials and methods of application will occur to those having skill in the art.

At the upper end of the housing 30, there may be provided a suitable connector 32 for electrically interconnecting the search unit with the transmitter-receiver. Such connector is of the type suitable for mating with the usual coaxial cable connector fitting. The body of the connector 32 may be metallic and constitute the ground for the cable in which event the body portion within the shell 30 may be electrically grounded to the shielding 31. Within the housing, a lead wire 37 extends from a center conductor of connector 32 and is connected to an electrode of the crystal as described more fully herein. Another electrode on the crystal is connected to the body of the connector via shielding 31 by a lead 36 soldered at junction 34 and extending downwardly therefrom to the crystal electrode. An inductance 35 may be added, here connected between junction 34 and the center conductor of connector 32 by a lead 33, for tuning the search unit to a desired reactance at the intended operating frequency.

Concentrically positioned within the shell 30 is an inner cylinder 40 which may be open at both ends and which has a length less than the length of the shell 30. The inner cylinder 40 is arranged and disposed within the shell 30 so that the forward end 41 of the cylinder projects beyond the forward edge of the shell 30 and terminates at a face 42. The cylinder has a diameter which is generally equal to the outside diameter of the crystal and supports the crystal at the end 41. The end 41 may be counterbored so as to form a downwardly facing shoulder 43 axially spaced from the face 42 of the cylinder a distance substantially equal to the thickness of the crystal.

The inner cylinder 40 defines what may be referred to as an inner potting cup and may be constructed of the same material as the outer shell 30. For example, the inner cylinder 40 may be formed from a paper based phenolic and, if desired, the outer surface of the cylinder 40 may be provided with a layer of shielding material such as baked on silver paint. The outer surface of the cylinder 40 may be provided with a vertical slot (not shown) so that the ground lead 36 may be disposed therein and run to the crystal face to which it is connected.

The piezoelectric ceramic crystal 50 may be of any desired shape, but is preferably a flat disc of uniform thickness so as to define upper and lower faces 51, 52, respectively, which are planar and parallel. The periphery of the crystal is cylindrical although the periphery may be beveled or chamfered at an angle in certain applications and constructions.

The crystal may be formed from conventional materials used for forming piezoelectric crystals such as lead zirconate titanate which has been found highly satisfactory in application. The front or lower face 52 of the crystal is provided with an electrode 53 which is a thin layer of electrically conductive material applied by any suitable means such as bonding a thin film onto the surface 52 with an electrically conductive cement, vapor depositing, or electroplating. The electrode 53 is electrically connected to lead wire 36.

The upper or rear face of the crystal 50 is also provided with an electrode 54 that is electrically connected to the lead wire 37. The front face of the crystal may be protected by a thin layer 55 of a compound comprising chopped fiberglass and epoxy resin which will increase the crack resistance and wearability of the front face of the crystal. The layer 55 may be applied by conventional methods for constructing a fiberglass layer such as hand layup or chopping which may be applied directly to the exposed surface of the electrode 53 or may be separately formed and secured to the electrode 53 with a suitable adhesive. It will of course also be understood that the layer 55 may be formed of other materials having resistance to chips or cracks and which has good abrasive qualities. The lower surface of the layer 55 defines the crystal wear face.

It is important to note that the wear face of the crystal 50 is flush or coplanar with the face 42 of the inner cylinder 40. In addition, the face of the crystal and the end 41 of the inner cylinder 40 are preferably about flush with the outer end of the outer shell 30. However, if desired the end 41 may project beyond the end of the outer shell 30.

Positioned between the inner cylinder 40 and the outer shell 30 of the search unit is a ceramic wear ring 60 having a forward end that projects beyond the forward end of the outer shell 30 and defines a wear face 62 that is substantially coplanar with the face 42 of the inner cylinder 40 and the face 56 of the crystal 50. The ceramic wear ring may be formed of a high density aluminum oxide which provides an extremely hard, durable, abrasion-resistant, protective ring that prevents wearing away of the crystal.

A ceramic of this variety has been found to be more wear resistant than the steel from which the outer shell of a search unit head is presently commonly constructed. As a result, it is not easily worn away. Accordingly, the peripheral edges of the crystal do not become exposed as described above.

The crystal 50 is securely mounted in the counterbored portion of the forward end of the inner cylinder 40 by any suitable means. By way of example, a suitable potting compound such as an epoxy resin may be used. Of course other means for securing the crystal in the inner housing may be used bearing in mind that it is desirable that the crystal be hermetically sealed to the inner cylinder 40. It is highly desirable to prevent any air spaces between the electrodes 53, 54 as such air space could allow an electric arc discharge to occur between the shielding material on the outer surface of the inner cylinder 40 and the electrodes.

After crystal 50 is mounted in the end of the inner cylinder 40, and wear ring 60 is in proper position, a dampening material 70 may be used to fill the cavity of the inner cylinder 40. The dampening material includes a binder such as a resin and preferably includes a heavy metal. Various types of dampening materials may be used such as the hard, rigid, dampening material disclosed in U.S. Pat. No. 2,972,068. Alternatively, a soft and more resilient and deformable dampening material may be used. An example of a dampening material of the latter type which has desirable characteristics are polyurethane resins of the low-foaming variety commonly used for casting and/or potting purposes, such as Scotchcast polyurethane resin No. 221 sold by Minnestoa Mining and Manufacturing Company.

After the cylinder 40 is filled with the potting compound 70 this subassembly including the ceramic ring 60 is secured in the housing 30. The void space is then filled with a suitable potting compound 71. A cap 72 may then be attached to the back of the search unit 12 for identification etc.

It will now be seen that an ultrasonic contact-type search unit 12 is provided in the present invention which has a wear face comprised of the end face 62 of the wear ring 60, and the wear face 56 attached to the crystal 50. The wear ring 60 greatly reduces wearing and protects the peripheral edge of the crystal against chipping or cracking.

The abrasion which usually occurs between the face of the search unit and the work surface is largely borne by the face 62 of the wear ring. Since this face is of an extremely hard and abrasion-resistant material, the life of the wear face of the crystal is greatly increased. Also the wear face material 55 may be of a relatively inexpensive material.

In addition it may be seen that the outer housing 30 in no way contributes to the wear characteristics of the search unit since the forwardmost edge or end of the housing 30 is recessed or set back from the wear face. As a consequence, it is no longer subject to serious wearing. Unlike a steel housing as used in prior art devices wherein the hardness of the steel is relied upon to provide a wear face that protects the crystal, the outer housing in the present invention in no way contributes to the wear characteristics of the unit and may thus be of an inexpensive, light-weight material as compared with steel. It will be apparent to those having skill in the art that variations and modifications of the search unit herein disclosed may be made without departing from the scope of the invention.

I claim:
1. An electro-acoustic ultrasonic search unit comprising:
   a generally cylindrical housing open at least at one end;
   an inner cylinder open at least at one end mounted within said housing;
   a piezoelectric crystal disc transducer mounted in said inner cylinder open end, one face of said crystal projecting beyond the end of said housing; and
   a ceramic wear ring disposed between said housing and said inner cylinder, one end of said ring projecting beyond the end of said housing and substantially coplanar with said crystal face so as to define a wear face for said search unit that is abrasion resistant.

2. The search unit of claim 1 additionally comprising a protective layer disposed on the front face of said crystal.

3. The search unit of claim 2 wherein said protective layer comprises a compound of chopped fiberglass and epoxy resin.

4. An electro-acoustic ultrasonic search unit comprising:
   a generally cylindrical electrically non-conducting shell open at least at one end;
   an electrically conductive, electromagnetic signal shielding coating on the inner surface of said shell;
   an inner cylinder open at least at one end mounted within said shell and formed of an electrically non-conductive material;
   a piezoelectric crystal disc mounted in the open end of said inner cylinder, the exposed face of said crystal projecting beyond the end of said shell; and
   a ceramic wear ring positioned around said inner cylinder and within said shell so that one end of said ring projects beyond the end of said shell and has an annular face which is substantially coplanar with the face of said crystal so as to define a wear surface for contact with a workpiece during use of said search unit.

5. The search unit of claim 4 wherein the exposed face of said crystal includes a protective layer disposed thereon.

6. The search unit of claim 4 wherein said unit additionally comprises a coaxial cable connector including a metallic connector body which constitutes the electrical ground and which is electrically connected to the shielding on the inner surface of said shell.

7. The search unit of claim 4, wherein said ceramic ring is formed of a high density aluminum oxide.

8. The search unit of claim 4 wherein said inner cylinder includes an electrically conducting electromagnetic signal shielding coating on the outer surface thereof.

9. The search unit of claim 8 wherein said inner cylinder has an inner diameter less than the diameter of said crystal disc and an outer diameter greater than the diameter of said crystal disc and has a counterbored portion at one end thereof having a diameter substantially equal to the diameter of said crystal disc and an axial depth substantially equal to the thickness of said disc, said counterbored portion receiving said disc for positioning and mounting thereof.

10. A search unit for an ultrasonic testing system, including:

a generally cylindrical housing having at least one open end;

a piezoelectric disc transducer mounted coaxially within said housing adjacent the open end thereof, said crystal having a front face projecting beyond the end of said housing for transmitting and/or receiving ultrasonic waves with respect thereto; and a ceramic wear ring disposed coaxially between said housing and said disc transducer and having a substantially uninterrupted front annular face disposed substantially coplanar with said front face of said transducer, whereby said ceramic wear ring provides at said front annular face a wear surface for protecting said transducer from abrasion during contact scanning.

* * * * *